United States Patent [19]

Stephens

[11] 4,393,142
[45] Jul. 12, 1983

[54] ASSAY METHOD AND REAGENT FOR THE DETERMINATION OF CHLORIDE

[75] Inventor: Thomas W. Stephens, Indianapolis, Ind.

[73] Assignee: American Monitor Corporation, Indianapolis, Ind.

[21] Appl. No.: 344,331

[22] Filed: Feb. 1, 1982

[51] Int. Cl.$^3$ .................... G01N 33/52; G01N 33/84
[52] U.S. Cl. ........................................ 436/125; 422/61
[58] Field of Search ....................... 23/230 B; 422/61; 252/408; 436/125

[56] References Cited

U.S. PATENT DOCUMENTS 4,092,115  5/1978  Rupe .................................. 436/125
4,278,440  7/1981  Law ................................... 436/125

FOREIGN PATENT DOCUMENTS 2153387  5/1973  Fed. Rep. of Germany .

*Primary Examiner*—Sidney Marantz
*Attorney, Agent, or Firm*—Marilyn L. Amick

[57] ABSTRACT

A colorimetric assay method and reagent composition for the direct, quantitative determination of chloride in fluids which may be performed directly on non-deproteinized samples and which utilizes a reagent comprised of 2,4,6-tripyridyl-s-triazine, mercuric ions, ferrous ions, and a sulfate salt in a sulfate or sulfonate buffer at a selected pH in the range of about 1.5 to 3.0.

8 Claims, No Drawings

ASSAY METHOD AND REAGENT FOR THE DETERMINATION OF CHLORIDE

BACKGROUND OF THE INVENTION

1. Field of the Invention

This invention relates to an assay method and reagent composition for determining chloride levels in fluids, and more particularly to a direct colorimetric method which avoids a requirement of removing protein from the samples.

2. Importance of Accurate and Reliable Chloride Measurements

Chloride is the major extracellular anion in human body fluids, and it is thus significantly important in maintaining proper water distribution, osmotic pressure, and normal electrolyte (anion-cation) balance in the human body. Low serum chloride values may be found with prolonged vomiting, extensive burns, metabolic acidosis, Addisonian crisis, and renal diseases. Elevated chloride values, on the other hand, are associated with dehydration, congestive heart failure, hyperventilation and urinary obstructions. Determination of chloride in sweat is useful in the diagnosis of cystic fibrosis, where the secretion of chloride in sweat may be up to five times as high as that of healthy individuals.

Because of the vitally important roles chloride ions play in the normal functioning of life processes, and in view of the effects of diseases and other body malfunctions on the amount of chloride ions in the body, it has long been recognized that it is necessary to be able to accurately and reliably determine or measure chloride levels in serum and other body fluids in order to aid the physician in proper diagnosis and treatment. In addition, it is correspondingly often necessary that such measurements are able to be made quickly in response to an urgent or emergency request from a physician. Moreover, the ever-increasing recognition by clinicians of the need for frequent chloride determinations requires that the assay method desirably be suitable for multiple-purpose automated laboratory equipment.

3. Description of the Prior Art

A variety of direct and indirect methods for measurement of chloride has been reported in the literature. These methods may be described as mercurimetric titration, coulometric-amperometric titration, ion-specific electrode techniques, and colorimetric methods. Although these methods represent the prior art through the years, each has had certain disadvantages. For example, titration procedures tend to be time-consuming, and they are especially burdensome when the sample must be subjected to deproteinization procedures or other pre-treatment steps. Coulometric and ion-specific electrode techniques require the use of specialized laboratory instrumentation and equipment of limited utility. Further, these methods do not readily lend themselves to automation. Colorimetric methods, however, do not require the use of such highly specialized equipment or instrumentation and, in general, are adaptable to automation.

The most widely used of the automated colorimetric methods is the mercuric thiocyanate method. Unfortunately, however, this method suffers from several drawbacks. First, the method is not linear, and thus multiple standards and cumbersome calibration curves must be used to obtain valid results. Non-linearity is a further problem when assaying chloride in urine samples, which often have chloride levels lower than the lowest calibrator used to prepare the curve. Moreover, the method uses high concentrations of hazardous mercury which must be disposed of as waste. Also, the thiocyanate has a greater affinity for bromide and iodide than for chloride, thereby causing serious interference when these ions are present in an assay for chloride specifically. Finally, most mercuric thiocyanate methods involve protein removal, usually by dialysis, which can introduce further errors into the assay.

In what might be considered to be the closest of the prior art, Fried et al. (J. Clin. Chem. Clin. Biochem. 10, 1972, p. 280) describe a colorimetric method for the direct determination of chloride using mercuric ions and the indicator 2,4,6-tripyridyl-s-triazine (TPTZ). Feldkamp et al. (J. Clin. Chem. Clin. Biochem. 12, 1974, pp. 146-150) describe the use of a colorimetric mercuric TPTZ method in studying interfering halides on continuous flow analyzers. De Jong et al. (Clin. Chem. 26, 1980, pp. 1233 and 1234) describe a modification of the Feldkamp method which is also utilized with continuous flow analyzers. The de Jong modification was reportedly made to overcome the shortcomings of the Feldkamp procedure. As stated on page 1233 of the de Jong publication, "The automated method of Feldkamp et al. . . . involving mercuric 2,4,6-tripyridyl-s-triazine (TPTZ) as proposed by Fried et al. . . . is excessively noisy owing to the very high dilution required by this sensitive reagent, is critically dependent on mercuric nitrate flow, and does not decrease the amount of mercury used. The method, however, is linear and neither iodide nor bromide react preferentially." In spite of the achievements of de Jong, the Feldkamp method described still suffers from several drawbacks, as now specified.

First, the method suffers from interference due to the presence of protein in the sample. Because of the very high sample dilutions used by these authors, the interference has presumably been minimized, but dialysis to separate the protein from the reaction is used by both Feldkamp and de Jong. Feldkamp tried to further avoid the protein problem by adding a fixed amount of albumin to the samples used in his study so that the effect from the protein would be identical in all samples tested. Fried did apply the mercuric TPTZ reaction to protein-containing samples, but he makes no mention regarding interference due to protein. Because of the high dilution ratios Fried used (1:860 and 1:1070), the protein effect is presumably minimized to at least some extent by diluting the protein out. With regard to the Fried publication, it should be pointed out that Fried discloses only the presence and concentration of two ingredients in the reagent he used, namely mercuric-TPTZ and ferrous sulfate. This limited disclosure would hardly enable the most highly skilled in the art to perform the assay described in the publication.

Furthermore, the reagent described by de Jong is reported to be stable for at least one month at room temperature. This would therefore require reagent preparation by the analyst each month, and would preclude the time-saving and convenience of obtaining the reagent in a commercially manufactured, shelf stable form.

Finally, because of the method's extreme sensitivity, samples to be assayed must either be diluted manually prior to performing the assay, or they must be diluted out as described by de Jong, that is, using two dialyzers in series, or by some other manipulative means.

SUMMARY OF THE INVENTION

Accordingly, it is therefore a general object of the present invention to provide a novel method and reagent for the colorimetric, quantitative determination of chloride in fluids. A more particular object of the present invention is to provide a method that uses the indicator TPTZ and which can be performed directly on fluid samples containing protein, thus avoiding the cost, effort and potential error of protein elimination steps. A further object is to provide a method which has a high linear range over which useful chloride results may be obtained without the need for multiple-point calibration. Yet a further object is to provide a chloride determination method which substantially eliminates interference from protein and other components present in biological fluids. Another object is to provide a reagent with extended stability. Still another object is to provide a method that is rapid and suitable for use with a variety of generally available automated laboratory instrumentation. These and other objects, features and achievements will become apparent to those skilled in the art in the light of the teachings herein set forth.

In its broadest aspect, this invention is directed to a method and a reagent for the direct measurement of chloride in fluids. The method utilizes a reagent which is comprised of TPTZ, mercuric ions and ferrous ions. The reagent further comprises at least one sulfate salt, preferably sodium sulfate and/or manganese sulfate, a sulfate buffer, and is acidified to a selected pH in the range of 1.5 to 3.0, preferably 1.6 to 2.4. The reagent composition is stable and retains its utility for more than a year at room temperature.

The method is carried out by combining the sample to be assayed directly with a quantity of the reagent. The reaction time is essentially immediate, and the absorbance of the final color developed is measured at a wavelength of about 600 nm. The amount of chloride in the sample is then determined by comparing the absorbance thus obtained with the absorbance obtained from a similar reaction between the reagent and a sample containing a known amount of chloride.

DESCRIPTION OF THE PREFERRED EMBODIMENTS

It has been found that chloride can be determined in a fluid sample by a novel method using a mercuric TPTZ reagent without the need for deproteinization of the sample. As hereinbefore pointed out, the prior art has disclosed the determination of chloride by an exchange mechanism using mercuric TPTZ to complex chloride ions, thereby releasing the TPTZ to form the violet ferrous TPTZ complex. By proper selection of reagent pH, acidification and buffering of the reagent using sulfate ions, the inclusion of a properly selected sulfate salt, and by the avoidance of the addition of ammonium ion, the goals and objects of the present invention are achieved.

The pH range over which the violet ferrous TPTZ complex is completely formed is reported in the literature to be 3.4 to 5.8. It is presumably for this reason that the lowest pH described by the prior art for the mercuric TPTZ reagent is 3. However, it has been discovered that a lower pH is desirable, and that by proper pH selection in the range of about 1.5 to 3.0, interference from protein and other ligands can be minimized without detrimentally affecting the sensitivity of the assay. It is believed that the increased hydrogen ion concentration at these lower pH's prevents the interfering terminal carboxyl groups and amino acid residues on the protein molecule, e.g. aspartate and glutamate, and free amino acids, free fatty acids, and mono, di, and tricarboxylic acids, e.g., lactic, citric and malic acids, from binding mercury and thus causing a positive interference in the method.

Further, it has been found that the presence of a high concentration of manganese ions further reduces the positive interference due to the presence of some ligands. It is believed that the manganese ions competitively bind up the interfering ligands while not binding significant amounts of chloride ion. The manganese ions are also beneficial in reducing the sensitivity of the reaction, which is useful when the analyst requires a lower sensitivity to meet the requirements of certain laboratory instrumentation.

The inclusion of a properly selected sulfate salt has also been found to provide beneficial effects. The sulfate ion is believed to provide a stabilizing effect on the composition. Where reduced sensitivity is desirable, the preferred salt is manganese sulfate. On the other hand, if a reagent with greater sensitivity is desired, sodium sulfate has been found to be the preferred sulfate salt. Magnesium sulfate and cupric sulfate have also been found to be useful.

It has been found that acidification and buffering of the reagent using sulfuric acid rather than nitric acid as taught by the prior art produces even further beneficial effects. As stated above, it is believed that the sulfate ion provides a stabilizing effect on the reagent composition. Nitrates and nitrites, formed by decomposition, tend to oxidize the ferrous ions present in the reagent, thereby exhibiting a deleterious effect with regard to reagent stability. Toluene sulfonate has also been found to be useful as a buffering agent.

Moreover, it has been found that the avoidance of ammonium ions as used in the de Jong prior art provides the beneficial effect of extending the linearity of the reaction, specifically on the low end of the range over which useful results can be expected.

EXAMPLE 1

A reagent was prepared with the following composition:
1.76 millimolar TPTZ
10 millimolar 1 N sulfuric acid
0.86 millimolar mercuric nitrate, monohydrate
0.42 millimolar ferrous sulfate, anhydrous
0.24 molar manganese sulfate, monohydrate The solution was brought to pH 1.6 using 1 normal sulfuric acid and was adjusted to an absorbance of 0.05 at 600 nm using a 0.2 molar mercuric nitrate solution before bringing the final volume to one liter with deionized water.

An assay for chloride was performed by combining 3.0 microliters of a serum sample and 0.6 milliliters of the reagent. The absorbance of the solution at 610 nm was then measured. The amount of chloride in the sample was determined by comparing the absorbance thus obtained with the absorbance of a similarly treated calibration material containing a known amount of chloride. In carrying out the assay of this example, the Parallel TM analyzer manufactured by American Monitor Corporation was utilized.

The selection of pH 1.6 and the inclusion of a high concentration of manganese ions result in a reagent with diminished sensitivity, thereby making it ideal for situations requiring a sample to reagent volume ratio of about 1:200. Examples of other instrumentation wherein the use of this reagent composition would be appropriate are the ABA 100 ™ bichromatic analyzer manufactured by Abbott Laboratories, the Multistat ™ analyzer manufactured by Instrumentation Laboratory, and various other semi-automated analyzers and bench-top spectrophotometers.

EXAMPLE 2

A reagent composition was prepared containing the following:
0.98 millimolar TPTZ
2.67 millimolar 1 N sulfuric acid
0.48 millimolar mercuric nitrate, monohydrate
0.44 millimolar ferrous sulfate, anhydrous
20.2 millimolar sodium sulfate, anhydrous The solution was brought to pH 2.4 with 1 normal sulfuric acid and was adjusted to an absorbance of 0.20 at 600 nm using a 0.2 molar solution of mercuric nitrate in 1 normal sulfuric acid before bringing the final volume to one liter with deionized water.

An assay for chloride was performed by combining 6.5 microliters of a serum sample and 4.0 milliliters of the reagent. The reaction was carried out at ambient temperature, and the absorbance of the solution at 610 nm was then measured. The amount of chloride in the sample was determined by comparing the absorbance thus obtained with the absorbance of a similarly treated calibration material containing a known amount of chloride. The KDA ® analyzer manufactured by American Monitor Corporation was utilized in performing the assay of this example.

The sample to reagent volume ratio used in this example is 1:666; however, the reagent composition of Example 2 is useful for ratios in the range of about 1:650 to 1:800. The reagent of this example would also be useful on instrumentation such as the AutoAnalyzer ™ manufactured by Technicon Instruments Corporation.

The adjustment of the absorbance of the reagent determines the linearity or useful range of the assay; and this absorbance is an empirically established value depending on the ratio of sample to reagent volume intended to be used in the assay. In general, the absorbance is adjusted downward until most of the TPTZ indicator is bound but a slight excess still remains. This enables the assay to be useful for determining low levels of chloride.

Although the invention has been illustrated by the preceding examples, it is not to be construed as being limited to the materials employed therein, but rather the invention encompasses the generic area as hereinbefore disclosed. Various modifications and embodiments thereof can be made without departing from the spirit and scope of the present invention.

For example, other indicators besides TPTZ may also be useful in the assay. It is believed that such other useful indicators, i.e., those of the type which form a colorless complex with mercuric ions and a colored complex with ferrous ions, must be of the tridentate type. Examples of such compounds include substituted phenanthroline, bipyridine, pyrazine, or triazine derivatives having an extended ferroin group.

What is claimed is:

1. A reagent composition for the determination of chloride in a protein-containing fluid, comprised of:
   (a) 2,4,6-tripyridyl-s-triazine;
   (b) mercuric ions;
   (c) ferrous ions;
   (d) at least one salt selected from the group consisting of sodium sulfate, manganese sulfate, magnesium sulfate, and cupric sulfate; and
   (e) a buffer selected from the group consisting of sulfuric acid and toluene sulfonate.

2. A composition as recited in claim 1, wherein the pH is between about 1.5 and 3.0.

3. A composition as recited in claim 1, wherein the pH is between about 1.6 and 2.4.

4. A method for the determination of chloride in a protein-containing fluid, comprising the steps of:
   (a) combining a sample of said fluid with a reagent to form a solution, said reagent comprising:
      (i) 2,4,6-tripyridyl-s-triazine,
      (ii) mercuric ions,
      (iii) ferrous ions,
      (iv) at least one salt selected from the group consisting of sodium sulfate, manganese sulfate, magnesium sulfate, and cupric sulfate; and
      (v) a buffer selected from the group consisting of sulfuric acid and toluene sulfonate;
   (b) measuring the absorbance of said solution; and
   (c) comparing the absorbance of said solution with the absorbance obtained on solutions containing known amounts of chloride.

5. A method as recited in claim 4, wherein the pH of said reagent is between about 1.5 and 3.0.

6. A method as recited in claim 4, wherein the pH of said reagent is between about 1.6 and 2.4.

7. A method as recited in claim 4, wherein the absorbance of said solution is measured at a wavelength between about 580 to 630 nm.

8. A test kit for the determination of chloride in protein-containing fluid samples, containing a reagent which comprises:
   (a) 2,4,6-tripyridyl-s-triazine;
   (b) mercuric ions;
   (c) ferrous ions;
   (d) at least one salt selected from the group consisting of sodium sulfate, manganese sulfate, magnesium sulfate, and cupric sulfate; and
   (e) a buffer selected from the group consisting of sulfuric acid and toluene sulfonate.

* * * * *